United States Patent [19]

Smith et al.

[11] 4,136,118

[45] Jan. 23, 1979

[54] METHOD OF PREPARING 2,2'-DITHIODIANILINE

[75] Inventors: Donald E. Smith, Tallmadge; Charles B. Jones, Akron, both of Ohio

[73] Assignee: The Goodyear Tire & Rubber Company, Akron, Ohio

[21] Appl. No.: 826,020

[22] Filed: Aug. 19, 1977

[51] Int. Cl.$^2$ .................... C07C 85/24; C07C 85/26
[52] U.S. Cl. .................... 260/578; 260/582; 260/608; 260/687 R; 260/705
[58] Field of Search .................... 260/578, 608, 306.5, 260/582

[56] References Cited

U.S. PATENT DOCUMENTS

| | | | |
|---|---|---|---|
| 1,933,217 | 10/1933 | Lantz | 260/578 X |
| 2,028,303 | 1/1936 | Turner | 260/578 X |
| 2,385,504 | 9/1945 | Goulding | 260/582 |
| 2,435,508 | 2/1948 | Paul et al. | 260/582 |

*Primary Examiner*—Winston A. Douglas
*Assistant Examiner*—John Doll
*Attorney, Agent, or Firm*—H. C. Young, Jr.

[57] ABSTRACT

Method of preparing 2,2'-dithiodianiline by the steps of (A) obtaining an agitated mixture of a water solution of a salt of o-aminothiophenol and an unstable dispersion therein of a liquid hydrocarbon, (B) oxidizing said salt by the slow addition of a water soluble peroxide, (C) discontinuing the agitation to allow the formation of a sharply defined lower aqueous phase and upper hydrocarbon phase, (D) drawing off said lower aqueous phase and (E) distilling the hydrocarbon phase therefrom and recovering said 2,2'-dithiodianiline as a distilland.

3 Claims, No Drawings

METHOD OF PREPARING 2,2'-DITHIODIANILINE

This invention relates to a method of preparing 2,2'-dithiodianiline.

The 2,2'-dithiodianiline is particularly useful for curing, crosslinking or extending isocyanate-terminated polyurethane prepolymers. It can be prepared by oxidizing the sodium salt of o-aminothiophenol. However, the 2,2'-dithiodianiline must be obtained in high purity form, without the attendant typical oxidation byproducts, for satisfactory use in the preparation of most cured polyurethanes.

Heretofore, 2,2'-dithiodianiline could be prepared by the steps of (A) oxidizing an aqueous solution of the sodium salt of o-aminothiophenol through the slow addition of hydrogen peroxide to form a water slurry of the water insoluble 2,2'-dithiodianiline, and solution of water soluble byproducts and (B) mixing toluene with the slurry to extract the 2,2'-dithiodianiline in the hydrocarbon phase.

However, such a method has particular disadvantages since the solid 2,2'-dithiodianiline product is directly subject to degradation by (A) rising to the top of the aqueous slurry during the reaction and being scorched, or oxidized, by contact with the hydrogen peroxide slowly being added, and (B) by being in direct contact with sodium hydroxide product in the aqueous phase. The 2,2'-dithiodianiline is simply subject to degradation by being in contact with both one of the reactants and by one of the products.

Therefore, it is an object of this invention to provide a method of preparing 2,2'-dithiodianiline through the oxidation of a salt of o-aminothiophenol and recovering the 2,2'-dithiodianiline in a relatively high purity form.

In accordance with this invention, a method of preparing 2,2'-dithiodianiline through the oxidation of a salt of o-aminothiophenol and recovering the 2,2'-dithiodianiline in a relatively high purity form is provided.

In accordance with this invention, a method of preparing 2,2'-dithiodianiline comprises the sequential steps of (A) obtaining an agitated mixture of a water solution of the sodium or potassium salt of o-aminothiophenol and an unstable dispersion therein of a liquid hydrocarbon selected from at least one of toluene, benzene or xylene, (B) oxidizing said salt of o-aminothiophenol by slowly adding a water soluble peroxide to said agitated dispersion to form products which comprise inorganic salts, sodium or potassium hydroxide and 2,2'-dithiodianiline, (C) discontinuing the agitation of the dispersion to allow the mixture to substantially immediately separate into a lower aqueous phase and upper hydrocarbon phase having a continuous, sharply defined innerface therebetween, (D) drawing off said lower aqueous phase and (E) distilling the remaining hydrocarbon phase to remove said hydrocarbon therefrom and recovering said 2,2'-dithiodianiline as a distilland.

In the preferred practice of this invention, the method of preparing the 2,2'-dithiodianiline comprises (A) forming an agitated, unstable mixture comprised of (1) 100 parts by weight of an aqueous solution comprising about 10 to about 50, preferably about 15 to about 30, weight percent sodium or potassium, preferably sodium, salt of o-aminothiophenol, and correspondingly, about 90 to about 50, preferably about 85 to about 70, weight percent water and (2) about 10 to about 50, preferably about 15 to about 25, weight percent hydrocarbon selected from at least one of toluene, benzene or xylene, preferably toluene, (B) oxidizing said salt of o-aminothiophenol by adding a water soluble peroxide, preferably hydrogen peroxide, to said agitated dispersion sufficiently slowly so that only a trace, if any, residual peroxide concentration is maintained in the dispersion, at a temperature in the range of about 5° C. to about 50° C., preferably about 10° C. to about 40° C., to form products including inorganic salts, sodium or potassium hydroxide and substantially water insoluble, yet hydrocarbon-soluble, 2,2'-dithiodianiline, (C) discontinuing said agitation to essentially immediately yield a sharply defined lower aqueous phase and an upper hydrocarbon phase containing said 2,2'-dithiodianiline essentially exclusive of the remainder of said products contained in said aqueous phase, (D) drawing off said sharply defined aqueous phase and (E) distilling the remaining hydrocarbon phase to a pot temperature in the range of about 130° C. to about 150° C. under a reduced pressure in the range of about 50 to about 200 millimeters (mm) of mercury to remove said hydrocarbon solvent as a distillate and recover said 2,2'-dithiodianiline as a distilland in a sufficient purity for an isocyanate-terminated polyisocyanate/polymeric polyol curative.

It is important to appreciate that it has been discovered that the practice of this invention especially enhances the stability and recovery of a relatively high purity 2,2'-dithiodianiline product by minimizing its contact with its degrading environment. The practice of this invention further enables larger batches to be produced in the same equipment utilized for the prior slurry process and, therefore, enables a general improvement in the overall process.

Indeed, the utilization of the unstable hydrocarbon/water solution dispersion effects both an effective insulation and clean separation of the 2,2'-dithiodianiline product in a relatively high purity form from the presence of degraded reactants and byproducts right at the point of reaction itself. As the reaction proceeds, the product is immediately both withdrawn from its reaction medium and insulated therefrom.

Generally, the 2,2'-dithiodianiline is uniquely of sufficiently high purity, without additional purification steps, to be satisfactorily used as a curative for some isocyanate-terminated polyurethane prepolymers although at least one water wash of the product is preferably for optimum results. It should readily be appreciated by those having skill in the polyurethane art that purity of reactants is of high priority in such polyurethane reaction systems.

For optimum purity of the 2,2'-dithiodianiline for use as a polyurethane curative, it is desired to water wash the hydrocarbon phase containing the 2,2'-dithiodianiline (before the distillation step) with at least one, generally from 1 to 5, preferably 2 to 4, water washes. The primary purpose is to remove traces of sodium or potassium hydroxide which can typically adhere to surfaces of the physical reactor system itself and bleed into the product or hydrocarbon phase contained in the reactor.

In the conduct of the reaction, it is necessary to provide an agitated, unstable aqueous solution/hydrocarbon dispersion. The liquid hydrocarbon is chosen so that it is naturally immiscible with the aqueous solution. Therefore, the mixture requires agitation, preferably a very rapid or high degree of agitation, to provide and maintain the dispersion. When the agitation stops, the dispersion disappears within a few minutes, typically in a minute or less, yielding sharply defined aqueous and hydrocarbon phases. Such agitation can be provided by conventional means.

In the further conduct of this invention, it is desired to minimize the potential of excess of the peroxide reactant. On this basis, (1) the peroxide is only added slowly for this purpose and to keep the reaction exotherm down and (2) a test is made to determine if the reaction is essentially complete so that further peroxide addition is not necessary. For this test, the agitation is stopped, the phases automatically separated, and a sample of the aqueous phase withdrawn and tested for peroxide content. If the sample does not contain peroxide, the agitation and dispersion are re-established and peroxide addition resumed. If the sample contains peroxide, the reaction is considered complete.

For the practice of this invention, the o-aminothiophenol can conveniently be obtained from the reaction of benzothiazole with sodium hydroxide. Such a reaction is generally exothermic and can be conducted at a temperature in the range of about 130° C. to about 170° C. The product of such a reaction is upgraded to remove impurities by first steam stripping to remove volatiles, aniline and benzothiazole, following which water and hydrocarbon are added to adjust the concentration of the sodium salt of o-aminothiophenol in the water to about 3 to about 30 weight percent. The mixture can be, if desired, treated with activated carbon to remove trace impurities and filtered. The o-aminothiophenol salt, as an aqueous solution in the presence of the hydrocarbon is now ready for oxidation.

The practice of this invention is further illustrated by reference to the following examples which are intended to be representative rather than restrictive of the scope of the invention. Unless otherwise indicated, all parts and percentages are by weight.

EXAMPLE I

To a suitable reactor was charged 1.2 parts of a 24 weight percent aqueous solution of the sodium salt of o-aminothiophenol and 1.5 parts toluene. The temperature of the mixture was adjusted to about 20° C. and rapidly agitated to form a dispersion which would be unstable if it were not for the agitation. To the rapidly stirred mixture and dispersion was then slowly added about 0.16 part by weight hydrogen peroxide as a 13.5 percent aqueous solution over a period of about 20 to 30 minutes. This amounted to about a 16 percent excess peroxide to insure complete oxidation. With stirring, the reaction system was maintained at a temperature in the range of about 20° C. to about 50° C., which was about a maximum allowable temperature, while the 2,2'-dithiodianiline product formed in the aqueous phase and immediately and exclusively withdrew and dissolved into the dispersed toluene phase.

The final oxidation product contained 2,2'-dithiodianiline in high purity form in the dispersed toluene phase while the water phase selectively contained reaction byproducts which included inorganic salt, sodium hydroxide as well as the original water.

Agitation was stopped and the mixture automatically and quickly separated into a shrply defined upper toluene phase and a lower aqueous phase in a few seconds to a few minutes. The lower aqueous phase was simply drawn off and separated from the toluene phase. The organic toluene phase was washed three times with about 8.3 parts by weight of water, with the water phase being drawn off after each wash. The parts by weight was based on one part by weight final 2,2'-dithiodianiline.

It is important to appreciate that the 2,2'-dithiodianiline product can be degraded by the sodium hydroxide. Therefore, the immediate extraction of the 2,2'-dithiodianiline product into the toluene phase during the actual reaction step has a very special value.

The toluene from the toluene phase was simply removed by flash distillation from the top of the reactor through a condenser into a receiver at a reduced pressure of about 100 millimeters mercury and a pot temperature of about 150° C. The remaining molten distilland product was removed from the reactor by pressurizing with about 5 psig nitrogen from the reactor at about 130° C. and packaged in containers in which it solidified when cooled below about 90° C. The overall yield was above 90 percent of 2,2'-dithiodianiline of a total amine content (purity) of about 98.1 percent.

The 2,2'-dithiodianiline product was then successfully used as a curative for an isocyanate-terminated polyisocyanate/polymeric polyol polyurethane prepolymer of toluene diisocyanate and polytetramethylene ether glycol.

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing 2,2'-dithiodianiline which comprises (A) forming an agitated, unstable mixture comprised of (1) 100 parts by weight of an aqueous solution comprising about 10 to about 50 weight percent sodium or potassium salt of o-aminothiophenol, and correspondingly, about 90 to about 50 weight percent water and (2) a dispersion therein of about 10 to about 50 parts by weight hydrocarbon selected from at least one of toluene, benzene or xylene, (B) oxidizing said salt of o-aminothiophenol by adding a water soluble peroxide to said agitated dispersion sufficiently slowly so that only a trace, if any, residual peroxide concentration is maintained in the dispersion, at a temperature in the range of about 5° C. to about 50° C., to form products including inorganic salts, sodium or potassium hydroxide and substantially water insoluble, yet hydrocarbon-soluble, 2,2'-dithiodianiline, (C) discontinuing said agitation to essentially immediately yield a sharply defined lower aqueous phase and an upper hydrocarbon phase containing said 2,2'-dithiodianiline essentially exclusive of the remainder of said products contained in said aqueous phase, (D) drawing off said sharply defined aqueous phase and (E) distilling the remaining hydrocarbon phase to a pot temperature in the range of about 130° C. to about 150° C. under a reduced pressure in the range of about 50 to about 200 millimeters of mercury to remove said hydrocarbon solvent as a distillate and recover said 2,2'-dithiodianiline as a distilland.

2. The method of claim 1 which comprises (A) forming an agitated mixture of (1) 100 parts by weight of an aqueous solution comprised of about 15 to about 30 weight percent sodium salt of o-aminothiophenol and, correspondingly, about 85 to about 70 weight percent water and (2) a dispersion therein of about 15 to about 25 parts by weight toluene, at a temperature in the range of about 10° C. to about 40° C., (B) oxidizing said sodium salt by slow addition of hydrogen peroxide to said agitated mixture, (C) discontinuing the agitation to form the sharply defined lower aqueous phase and upper hydrocarbon phase, (D) drawing off said aqueous phase, (E) distilling the hydrocarbon phase to recover 2,2'-dithiodianiline as a distilland in a sufficient purity for an isocyanate-terminated polyisocyanate/polymeric polyol curative.

3. The method of claim 2 where, as the water soluble hydrogen peroxide is slowly added to the unstable mixture, which is sufficiently agitated to maintain a dispersion of the toluene, the 2,2'-dithiodianiline is immediately withdrawn from its aqueous reaction medium into the dispersed toluene and insulated therefrom.

* * * * *